United States Patent [19]

Nogami

[11] Patent Number: 4,781,456
[45] Date of Patent: Nov. 1, 1988

[54] ABSORPTION PHOTOMETER
[75] Inventor: Taro Nogami, Katsuta, Japan
[73] Assignee: Hitachi, Ltd., Tokyo, Japan
[21] Appl. No.: 76,212
[22] Filed: Jul. 22, 1987
[30] Foreign Application Priority Data Jul. 26, 1986 [JP] Japan .................. 61-176467

[51] Int. Cl.$^4$ .................. G01J 3/427
[52] U.S. Cl. .................. 356/51; 356/320; 356/328
[58] Field of Search .................. 356/51, 320, 326, 328, 356/331, 332, 334

[56] References Cited

U.S. PATENT DOCUMENTS

| | | | |
|---|---|---|---|
| 3,218,914 | 11/1965 | Bartz et al. | 356/320 |
| 3,279,308 | 10/1966 | Bartz et al. | 356/51 |
| 3,519,816 | 7/1970 | Bartz et al. | 356/51 |
| 3,554,649 | 1/1971 | Ridgway | 356/334 |
| 4,022,531 | 5/1977 | Orazio et al. | 356/332 |
| 4,140,394 | 6/1977 | Roos | 356/306 |
| 4,289,401 | 12/1979 | Mohr | 356/305 |
| 4,557,601 | 12/1985 | Kuroishi et al. | 356/320 |

FOREIGN PATENT DOCUMENTS

| | | | |
|---|---|---|---|
| 0045898 | 2/1982 | European Pat. Off. | 356/320 |
| 0117118 | 6/1985 | Japan | 356/320 |
| 62-50641 | 3/1987 | Japan | |

OTHER PUBLICATIONS

Mavrodineanu et al., *Applied Optics*, vol. 7, No. 7, Jul. 1968, pp. 1281–1285.

Primary Examiner—F. L. Evans
Attorney, Agent, or Firm—Antonelli, Terry & Wands

[57] ABSTRACT

An absorption photometer for measuring the absorption by conducting the light to a thin flow cell in which a liquid sample flows, wherein the sample light for measuring the absorption peak is superimposed on the reference light selected from the transparent (window) range of the liquid and the absorbance is detected by separating the sample light and reference light after transmission of the flow cell. Changes in the light path conditions can be monitored accurately, and therefore high-accuracy measurement immune to noises is made possible even using an elongated flow cell.

11 Claims, 6 Drawing Sheets

ABSORPTION PHOTOMETER

BACKGROUND OF THE INVENTION

1. Field of the Invention

This invention relates to an absorption photometer, and particularly to an absorption photometer suitable for the photometric analysis in which a small amount of sample is fed through a flow cell and the transmitted light is measured.

2. Description of the Prior Art

Absorption photometers are used in various analytical instruments. Among those instruments, typical ones which implement the measurement by feeding a liquid sample through a flow cell are the liquid chromatograph analyzer, flow injection analyzer, and automatic biochemical analyzer for clinic. The flow injection analysis is described, for example, in U.S. Pat. No. 4,557,601, which is hereby incorporated by reference.

For the measurement of a sample which is fed through a flow cell, it is important to know the composition (or variation of composition) of the sample which is being fed through the flow cell at that time point. Samples for measurement are given as solutions in carriers such as water or organic solvent. The measuring wavelength is set to the typical absorption peak of one compound and the variation of absorption at that wavelength is measured as a function of time. In case there is no absorption, the amount of light incident to the detector must have been known in order to attain a sufficient measurement accuracy. The amount of incident light to the detector varies depending on the variation in the power voltage, ambient temperature and light source position. For compensating the light source variations, a beam splitter is placed between the light source and flow cell to monitor the output light. However, such a monitoring method does not completely eliminate the variation of base line in the measurement result. For example, during the absorbance or optical density measurement, a signal indicating as if the absorption increases or decreases is generated even though there is no change in the sample. Accordingly, it is desired to perform the measurement which provides a signal solely based on the true absorption of the sample.

SUMMARY OF THE INVENTION

This invention is intended to overcome the prior art deficiencies, and its prime object is to provide an absorption photometer which performs stable measurement invariably even if the light source point moves, the optical axis shifts due to the inhomogeneity of air, or the density of sample liquid within the sample cell varies.

According to one aspect of this invention, there is provided an absorption photometer which comprises a light source, dispersion means for dispersing lights according to the wavelengths, light incident means located between the light source and dispersion means for making the light output from the light source incident as at least two beams of different incident angles into the dispersion means, means for taking out the light output from the dispersion means in one diretion and making the light incident to the sample in the sample cell, detection means for detecting the transmitted light through the sample for at least two wavelengths independently, and an arithmetic operation means for calculating the ratio of the detection results at different wavelengths provided by the detection means.

When a dispersion means is arranged to receive the light in two directions and output the light in one direction, it provides a single light beam including more than one wavelength component. The produced light beam is made incident to the sample cell and the transmitted light is detected for more than one wavelength independently. Among two light beams with different wavelengths, one is set for use as a sample light to have the absorption wavelength of the substance under measurement within the sample liquid, while the other is set for use as a reference light to have a wavelength free from absorption by the substance under measurement. Although the reference light is not absorbed by the substance under measurement, it is subjected to the same variation as of the measurement light in terms of the variation in the light source intensity and the shift of the light path and optical axis in the cell, allowing the detection of these variations.

The means for making the light incident at different incident angles into the dispersion means is constituted, for example, by a beam splitter optical system and more than one incident slit having an equal light path length to the dispersion means. The means for taking out the light from the dispersion means in a single direction is constituted, for example, by an output slit. Light beams with an equal exit angle, but with different incident angles, have different wavelengths. Accordingly, by choosing an exit angle and more than one incident angle, a single light beam including light components of different wavelengths is produced. These different wavelength components enable the separation of the light intensity variation caused by changes in factors other than the absorption of sample, such as the light source variation, voltage variation and flow cell density variation, from the light intensity variation caused by a change in the component concentration of the sample.

According to another aspect of this invention, there is provided an absorption photometer which comprises a light source, a diffraction grating for diffracting the first-order diffraction light in the visual range and the second-order diffraction light in the ultraviolet range, means for taking out the diffracted lights from the grating in a single direction and making the lights incident to the sample in the sample cell, detection means for detecting the transmitted light through the sample for at least two different wavelengths independently, and an arithmetic operation means for comparing the results of detection at different wavelengths provided by the detection means.

The diffraction grating disperses high-order lights invariably in the same direction as the first-order light, and therefore a light beam including more than one wavelength can be produced without using a special device. Usually, when the absorption is measured using the second-order light, the first-order (and the third and higher order lights if necessary) is removed with a filter, prism, or the like. The second aspect of this invention enables independent measurements at two wavelengths through the positive use of both the first and second-order lights.

DESCRIPTION OF THE PREFERRED EMBODIMENTS

Figure 1:
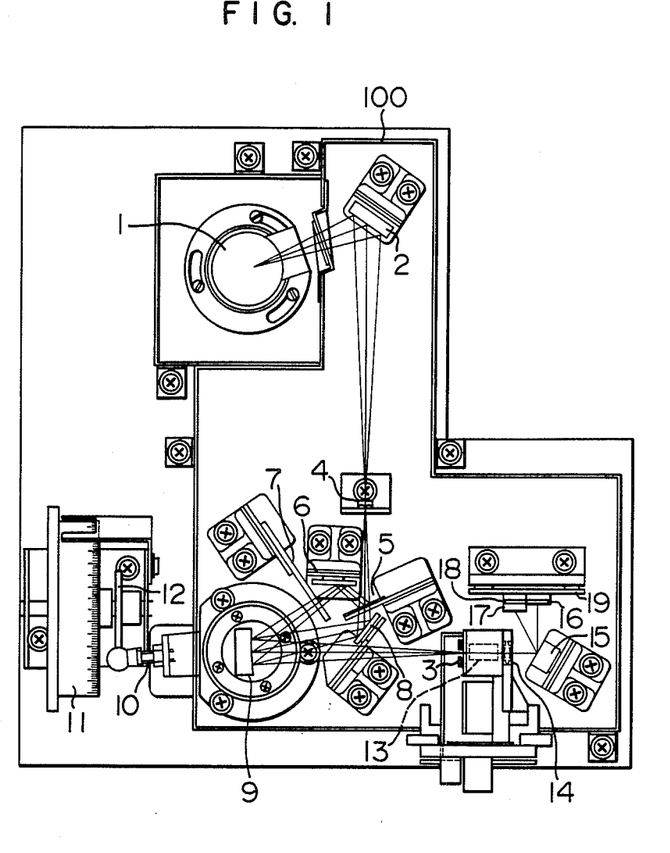
FIG. 1 is a plan view of the absorption photometer which is the first embodiment of the present invention.

FIG. 1 shows in plan view the first embodiment of the inventive absorption photometer, in which reference number 1 denotes a light source, e.g., deuterium ($D_2$) lamp, 2 is a condensor mirror having a toroidal surface for example, 4 is an incident slit, 5 is a beam splitter, e.g., semi-transparent mirror, 6 and 8 are planar mirrors, 7 is a short-cut filter for transmitting the light above a certain wavelength, 9 is a concave diffraction grating, 3 is an output slit, 10 is a wavelength bar, 11 is a dial, 12 is a wavelength cam, 13 is a flow cell in which a liquid sample is fed for the continuous measurement, 15 is a diffraction grating, 16 is a measuring detector, 17 is a short-cut filter, 18 is a reference detector, and 19 is a signal processing circuit. A condenser lens 14 may be inserted immediately after the flow cell 13. A light shield 100 is provided in the exterior of the light path.

In the absorption photometer, the light from the light source 1 is condensed by the condensor mirror 2, and it is entered through the incident slit 4 into the spectrometer. The main light beam is reflected by the planar mirror 8, and, after being entered at a smaller incident angle and dispersed by the concave grating 9, the light with a specific wavelength goes through the output slit 3. Part of the light is directed apart from the main light beam by means of the beam splitter 5 in the spectrometer, and, after being incident through the mirror 6 and short-cut filter 7 to the concave grating 9 at a larger incident angle and dispersed by it, the light above the above-mentioned specific wavelength goes through the output slit 3.

For a grating, there is given for the first-order diffraction light a functional relationship between the light wavelength $\lambda$, grating incident angle $\alpha$, diffraction angle $\beta$ and grating constant d, as follows: $\sin \alpha + \sin \beta = \lambda/d$. In FIG. 1, the incident angles $\alpha_1$ and $\alpha_2$ and output angle $\beta$ are all positive, and the output light from the output slit 3 includes two kinds of light. Since $\beta$ is common, the light with the greater incident angle will have a longer wavelength. With the incident angles $\alpha_1$ and $\alpha_2$ ($\alpha_1 < \alpha_2$) being made correspondence to wavelengths $\lambda_2 = 250$ nm and $\lambda_2 = 400$ nm, respectively, the angles $\alpha_1$, $\alpha_2$ and $\beta$ are chosen.

The light which has passed through the output slit 3 is directed to the flow cell 13. The flow cell 13 has a flow of liquid, and the concentration of a certain component in the liquid is measured continuously. When the sample is little in quantity, a flow cell with a smaller inner diameter is preferably used. However, it is difficult for a flow cell with a smaller inner diameter to maintain the light path in the cell, and the measuring wall of the cell is prone to cut part of the light beam. When a single light beam including more than one wavelength is conducted through the flow cell to implement monitoring using a wavelength free from absorption, the variation in the amount of light can be corrected even in the aforementioned case. This allows the use of a flow cell of 0.4 mm in inner diameter and 1 cm in length. The need of using a cell shorter than 1 cm in reference length with the intention of maintaining the light path is reduced significantly. Behind the flow cell 13, there is disposed a diffraction grating 15. A lens 14 may be provided so that the condensed light is incident to the grating 15.

In this embodiment, the grating 15 plays two roles. One is to diffract the zero-order light in the same way as mirror reflection, and the other is to disperse the light (particularly first-order dispersion) depending on the wavelength. The measuring light coming by way of the mirror 8 undergoes first-order diffraction, and it is received by the measuring detector 16. The reference light coming by way of the mirror 6 and short-cut filter 7 undergoes zero-order diffraction (reflection), and it is fed through the short-cut filter 17 and received by the reference detector 18. The use of the zero-order light is advantageous in the efficiency of energy, and it also allows a greater angle between the measuring light and reference light. The measuring light has its zero-order light diffracted in the same direction, but it is removed by the shortcut filter 17. The detector is constituted, for example, by a silicon photocell, or otherwise a photo-multiplier, phototube, or the like may be employed for it. A concave grating with a short focal distance may be used for the grating 15, and in this case the lens 14 is unused. The reference detector may be placed at the position of receiving the first-order dispersion light of the reference light, instead of placing it at the position of receiving the zero-order light. In this case, dispersed lights are received and the shortcut filter 17 may be unused. The reference detector and measuring detector may be integrated to form a pair cell so that the number of component parts is reduced. Particularly, when two light spots to be detected are close to each other, disposition of component parts is facilitated.

Figure 2:
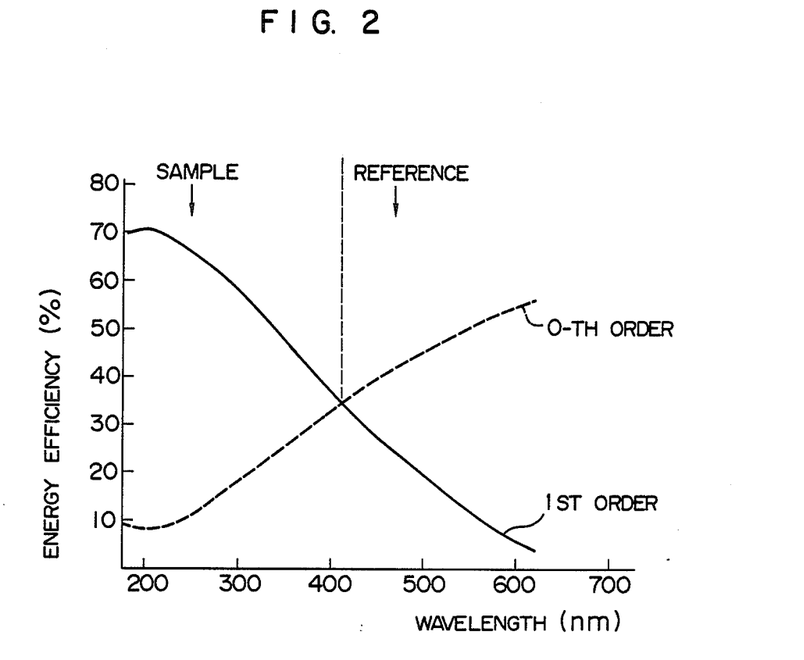
FIG. 2 is a graph used to explain the principle of the first embodiment.

FIG. 2 is pertinent to the detection system of the embodiment shown in FIG. 1 including the grating 15, measuring detector 16 and reference detector 17, explaining the reason for the reception of the first-order diffraction light with the measuring detector 16 and the reception of the zero-order light with the reference detector 17. The energy efficiency (%) is plotted on the ordinate versus the wavelength (nm) on the abscissa. The grating 15 is assumed to have its blaze wavelength set to somewhere about 200 nm. The first-order diffraction light has a higher energy efficiency in the ultraviolet range centered by about 200 nm. As the wavelength increases, the energy efficiency of the first-order diffraction light falls. The zero-order light has its energy efficiency rising with the increase in the wavelength. In many cases, the zero-order light has a higher energy efficiency in the visual range. The reference light is set to have a sufficiently longer wavelength (e.g., 100–300 nm) relative to the measuring light. In case the zero-order light has a higher energy efficiency than the first-order light at the reference light wavelength, it is advantageous to use the first-order diffraction light for the measuring light and the zero-order light for the reference light. On this account, preferably, the measuring light is set to have a wavelength somewhere about the absorption peak wavelength of the substance under measurement and the reference light is set to have a wavelength longer by 100–300 nm than the measuring light where the absorption by the substance under measurement is negligible.

Figure 3A:
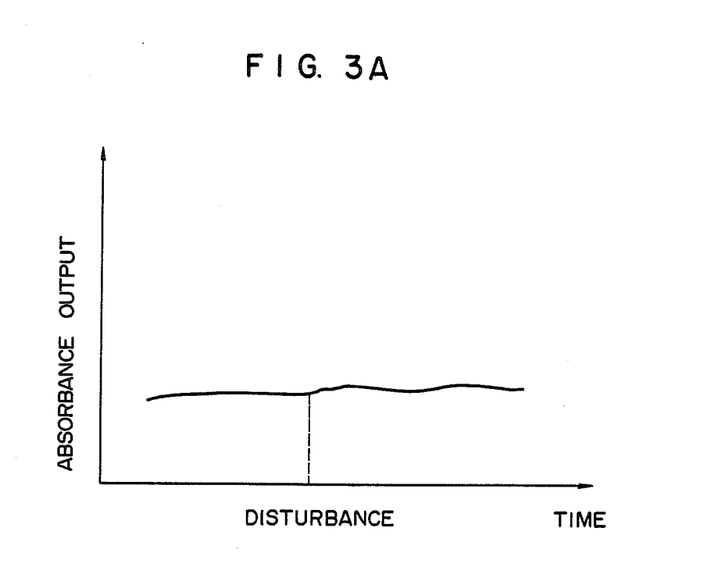
FIGS. 3A and 3B are graphs comparing the effectiveness of the inventive photometer with the conventional one.
Figure 3B:
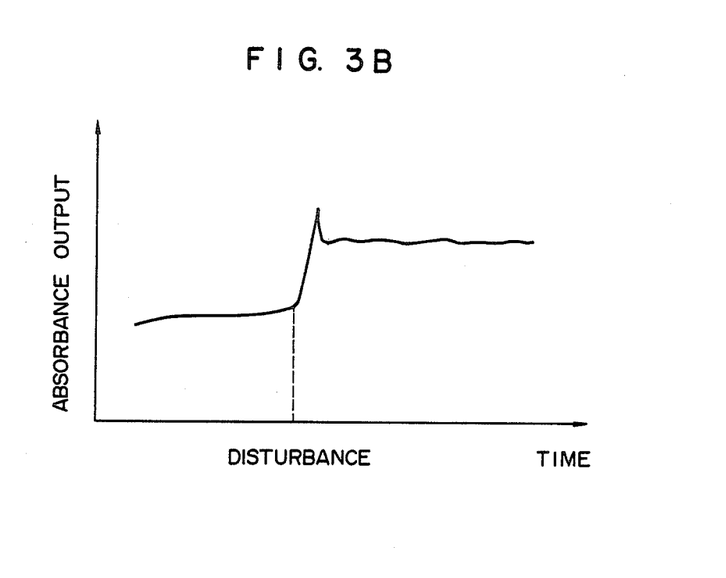

FIGS. 3A and 3B show the effect of correction by the light beam monitor. The absorbance output is plotted on the ordinate versus the time on the abscissa. FIG. 3B is the case without correction for the downstream portion after the flow cell, while FIG. 3A is the case with correction for the downstream portion after the flow cell. For example, a possible matter is that the liquid flowing in the flow cell has its refractive index varied due to changes in the pressure, temperature and the like caused by changes in the mixing ratio and flowrate, resulting in the variation of the optical axis, and thence in the variation in the amount of light on the detector. If correction is not conducted, a change in the base line as shown in FIG. 3B will arise in the measurement of absorption. The absorption photometer which also monitors changes inside the flow cell as mentioned above is subjected to virtually equal changes for the measuring light and reference light. The output signal of the measuring light calibrated by the reference light is modified as shown in FIG. 3A.

Also in the case of the positional variation of the light source or the shift of optical axis caused by the inhomogeneity of air, which arises often with such a light source using the arc discharge as a $D_2$ lamp, the foregoing absorption photometer is capable of accurately correcting the variation, since the reference light goes through the flow cell as the measuring light does. In another case where the reference light does not go through the flow cell, but is projected to a detector by way of another slit or the like, it is difficult to reproduce the same condition a the flow cell and to make a fine adjustment for the positional correspondence between the flow cell and the slit on the part of the reference light.

Figure 4:
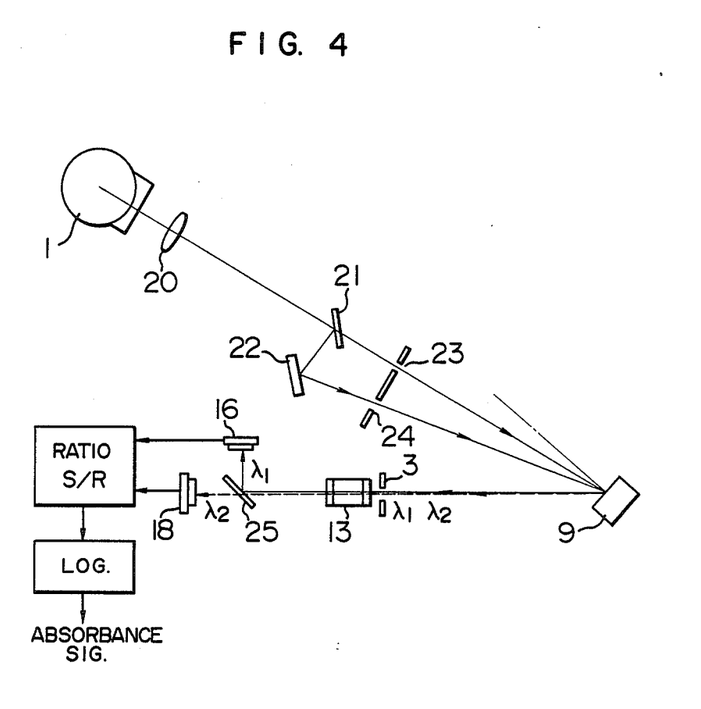
FIGS. 4, 5 and 6 are diagrams showing the optical systems according to the second, third and fourth embodiments of this invention.

FIG. 4 shows the optical system for explaining the second embodiment of this invention. Besides the component parts similar to those of FIG. 1 as referred to by similar symbols, the system includes a lens 20, a beam splitter 21, a mirror 22, a first incident slit 23, a second incident slit 24, a beam splitter 25, a band-pass filter 26, and a short-cut filter 27. In the absorption photometer of this embodiment, the light from the light source 1 is condensed by the lens 20. After being split by the beam splitter 21, two light beams enter the spectrometer by way of the first incident slit 23 and second incident slit 24. The beams are dispersed by the concave grating 9, and two kinds of dispersion lights are distributed. Among the dispersed lights of the light incident through the first incident slit 23, the light with a specific wavelength ($\lambda_1$) goes through the flow cell 13 by way of the exit slit 3. The light beam split by the beam splitter 21 is reflected by the mirror 22, and it irradiates the second incident slit 24. In case the lens 20 has the chromatic aberration, a longer wavelength light has a longer focal distance. In the optical system of FIG. 4, the fact that the second light beam going through the beam splitter 21 and mirror 22 has a longer light path than that of the first light beam can also be utilized positively for the correction of chromatic aberration. The second light beam is incident to the concave grating 9 at an incident angle different from that of the first light beam entering through the first incident slit, and it supplies the light with a wavelength ($\lambda_2$) different from the measuring wavelength $\lambda_1$ to the flow cell 13 by way of the exit slit 3. In the disposition of FIG. 4, $\lambda_2$ is larger in value, i.e., longer wavelength, than $\lambda_1$. The light beams with two distinct wavelengths passing through the flow cell 13 are divided by the dichroic mirror 25 of dielectric multi-layer films so that the light with the shorter wavelength $\lambda_1$ is reflected and the light with the longer wavelength $\lambda_2$ is transmitted. A band-pass filter or the like may be used in conjunction. The light with wavelength $\lambda_2$ which has passed through the dichroic mirror 25 is incident to the reference detector 18. Both detectors 16 and 18 have their output signals fed to a ratio calculator 102, in which the sample signal S is divided by the reference signal R, and the resulting S/R signal is sent to a logarithmic converter 104. The logarithmic converter 104 produces the absorbance signal given by $\log_{10}(I_o/I) = C \log(S/R)$, where $I_o$ is the incident light intensity and $I$ is the transmitted light intensity.

Instead of separating lights with two kinds of wavelengths using the dichroic mirror and filter after transmission through the flow cell, they can also be separated using a diffraction grating or prism.

Figure 5:
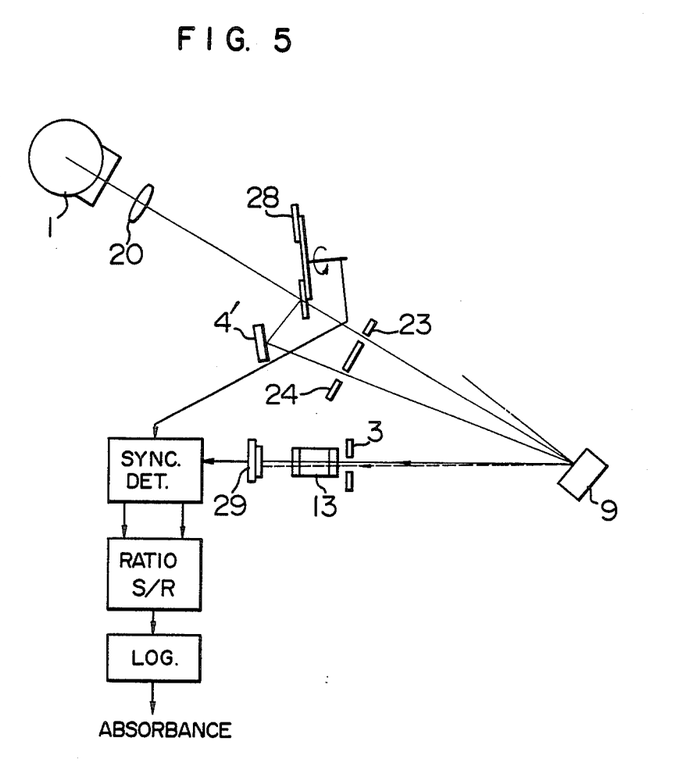

FIG. 5 shows the optical system according to the third embodiment of this invention. Besides the component parts similar to those in FIGS. 1 and 4 as referred to by similar symbols, the system includes a sector mirror 28 and a detector 29. In this embodiment, the beam splitter 21 used in the second embodiment of FIG. 4 is replaced with the sector mirror 28, and the light is distributed to the first incident slit 23 and second incident slit 24 on a time slice basis. In this case, the flow cell 13 is followed in its rear by the sole detector 29, which provides an output signal indicative of the measurement signal and reference signal alternately. These signals can be extracted separately by sampling each signal synchronously with the sector mirror 28 by means of a synchronous detection circuit 108 such as a lock-in amplifier.

Figure 6:
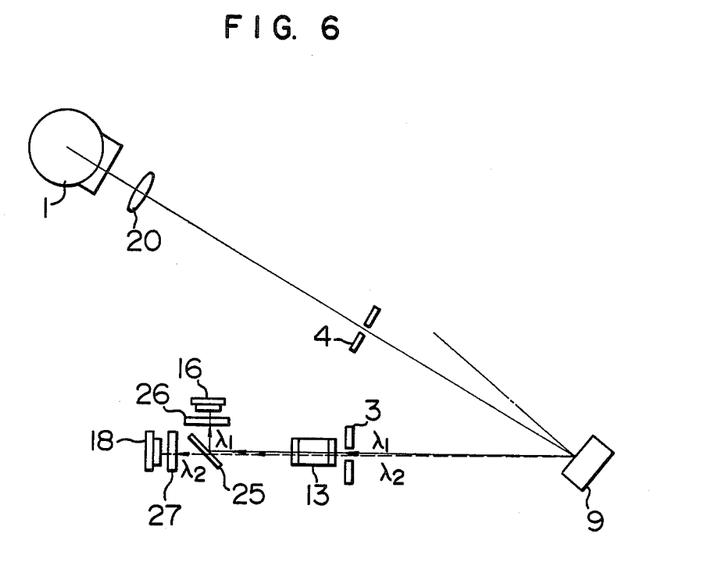

FIG. 6 shows the optical system according to the fourth embodiment of this invention. In the figure, component parts similar to those in FIGS. 1, 4 and 5 are referred to by similar symbols. In this embodiment, the light beam is not split at all before it reaches the flow cell 13, and the light coming through the incident slit 4 is simply analyzed and fed toward the flow cell 13 by way of the output slit 3. The concave grating 9 has a blaze wavelength in the long wavelength range above 400 nm so that the second-order diffraction light with wavelength $\lambda_1$ in the ultraviolet range and the first-order diffraction light with wavelength $\lambda_2$ in the visual range pass together through the flow cell 13. After passing through the flow cell 13, the light with each wavelength is extracted. The light reflected upward by a beam splitter 25 such as a semi-transparent mirror is conducted through a combination filter 26 made up of a band-pass filter and color glass filter so that only the light with wavelength $\lambda_1$ is selected. Another light beam split by the beam splitter is fed through a short-cut filter 27 so that the second-order light is removed. When the presence of high-order lights does not matter, the color glass filter may be omitted.

According to the absorption photometers described in the foregoing embodiments, the variation arising from a cut of light as being interrupted partially by the interior wall of the flow cell can be corrected through the monitoring at a downstream portion after the flow cell. Accordingly, even if the light source spot moves, the optical axis shifts due to the movement of air or the density of liquid in the flow cell varies, the stable measurement is promised invariably.

Although liquid chromatograph has been explained as an example, the present invention is not confined to this. The inventive photometer is particularly effective for the optical measurement using a flow cell in which liquid flows. For the light source, a tungsten lamp, metallic halide lamp or the like can be used selectively for each purpose.

I claim:

1. An absorption photometer comprising:
   a light source for emitting light in one wavelength range;
   a variable-wavelength spectrometer including dispersion means for dispersing the light depending on the wavelength;
   light directing means located between said light source and said dispersion means for producing more than one light beam from the light emitted by said light source and making the light beams incident to said dispersion means at different angles;
   means for taking out output light having different wavelengths from said dispersion means in one direction and for making the output light of different wavelength simultaneously incident to a sample in a sample cell;
   detection means for simultaneously detecting each light of different wavelength transmitted through said sample; and
   an arithmetic operation means for calculating the ratio of detection results at different wavelengths provided by said detection means.

2. An absorption photometer according to claim 1, wherein said dispersion means comprises a diffraction grating.

3. An absorption photometer according to claim 1, wherein said sample cell comprises a flow cell in which a liquid sample is fed.

4. An absorption photometer according to claim 1, wherein said light directing means comprises a beam splitter and mirrors, and wherein said detection means comprises means for separating the light of different wavelengths trnsmitted through said sample depending on each wavelength and more than one detector for respectively detecting the separated light.

5. An absorption photometer according to claim 4, wherein said means for separating the light of different wavelengths transmitted through said sample depending on each wavelength comprises a dielectric multilayer dichroic mirror which reflects the light with one wavelength and transmits the light with another wavelength.

6. An absorption photometer according to claim 1, wherein said detection means comprises a diffraction grating and two detectors, said detectors being disposed on the light path of the zero-order diffraction light and light path of the dispersion light of said diffraction grating, respectively.

7. An absorption photometer according to claim 6, wherein said detection means further comprises a short-cut filter disposed in front of said detector located on the light path of the zero-order diffraction light.

8. An absorption photometer according to claim 1, wherein said detection means comprises a diffraction grating and two detectors, said detectors being disposed at different angular positions with respect to the dispersing direction of said grating.

9. An absorption photometer comprising:
   a light source capable of emitting light in one wavelength range;
   a diffraction grating which disperses by diffraction the light in the visual range as a first-order diffraction light and the light in the ultraviolet range as a second-order diffraction light;
   means for taking out the dispersion light having different wavelengths from said grating in a single direction and for making the light of different wavelengths simultaneously incident to a sample in a sample cell;
   detection means for separately and simultaneously detecting the light of different wavelengths transmitted through said sample depending on each wavelength; and
   an arithmetic operation means for calculating the ratio of detection results at different wavelengths provided by said detection means.

10. An absorption photometer according to claim 9, wherein said sample cell comprises a flow cell in which a liquid sample is fed.

11. An absorption photometer according to claim 9, wherein said detection means comprises a beam splitter for separating the incident light into two light beams, a band-pass filter and a detector placed on the light path of one of the two separated light beams, and a short-cut filter and another detector placed on the light path of another light beam.

* * * * *